United States Patent
Kaku

(10) Patent No.: US 9,554,693 B2
(45) Date of Patent: Jan. 31, 2017

(54) IMAGE PROCESSING DEVICE

(75) Inventor: Toshihiko Kaku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 680 days.

(21) Appl. No.: 13/283,402

(22) Filed: Oct. 27, 2011

(65) Prior Publication Data

US 2012/0154565 A1 Jun. 21, 2012

(30) Foreign Application Priority Data

Dec. 16, 2010 (JP) ................. 2010-280630

(51) Int. Cl.
*A61B 1/06* (2006.01)
*A61B 1/00* (2006.01)

(52) U.S. Cl.
CPC .......... *A61B 1/0638* (2013.01); *A61B 1/00009* (2013.01); *A61B 1/0646* (2013.01); *A61B 1/0669* (2013.01); *A61B 1/063* (2013.01)

(58) Field of Classification Search
CPC .............. G02B 17/086; G02B 17/0848; G02B 2027/0178; G02B 27/0172; G02B 3/14
See application file for complete search history.

(56) References Cited

U.S. PATENT DOCUMENTS

| | | | |
|---|---|---|---|
| 5,282,030 A | 1/1994 | Nishimura et al. | |
| 8,451,328 B2 * | 5/2013 | Yoshino et al. | 348/65 |
| 8,500,632 B2 * | 8/2013 | Gono | A61B 1/00186 356/317 |
| 8,531,512 B2 * | 9/2013 | Gono | A61B 1/0638 348/131 |
| 2003/0153811 A1 | 8/2003 | Muckner | |
| 2003/0176768 A1 | 9/2003 | Gono et al. | |
| 2007/0046778 A1 | 3/2007 | Ishihara et al. | |
| 2007/0153542 A1 * | 7/2007 | Gono | A61B 1/0638 362/574 |
| 2008/0021272 A1 * | 1/2008 | Doguchi et al. | 600/109 |
| 2008/0262297 A1 * | 10/2008 | Gilboa et al. | 600/109 |

(Continued)

FOREIGN PATENT DOCUMENTS

| | | |
|---|---|---|
| EP | 2 105 082 A1 | 9/2009 |
| JP | H-4-183430 A | 6/1992 |

(Continued)

OTHER PUBLICATIONS

European Search Report dated Apr. 2, 2012.
Notification of Reason(s) for Refusal dated Apr. 23, 2013, with English translation.

*Primary Examiner* — Dave Czekaj
*Assistant Examiner* — Kehinde O Abimbola
(74) *Attorney, Agent, or Firm* — McGinn IP Law Group, PLLC

(57) ABSTRACT

An image processing device includes an image acquisition unit for acquiring a normal light observation image captured with white light and a special light observation image captured simultaneously with the normal light observation image using predetermined narrowband light, and an image processing unit for subjecting the normal light observation image acquired by the image acquisition unit to predetermined processing to generate a processed normal light observation image and providing information of the processed normal light observation image to the special light observation image.

5 Claims, 7 Drawing Sheets

(56) References Cited

U.S. PATENT DOCUMENTS

| | | | |
|---|---|---|---|
| 2008/0281154 A1 | 11/2008 | Gono et al. | |
| 2008/0287783 A1* | 11/2008 | Anderson | 600/429 |
| 2008/0294105 A1 | 11/2008 | Gono et al. | |
| 2008/0306338 A1 | 12/2008 | Yamazaki et al. | |
| 2009/0082625 A1* | 3/2009 | Gono | A61B 1/00186 600/109 |
| 2009/0149706 A1* | 6/2009 | Yamazaki et al. | 600/109 |
| 2010/0157038 A1 | 6/2010 | Hitokata | |
| 2010/0194933 A1* | 8/2010 | Sasaki | 348/241 |
| 2010/0225821 A1* | 9/2010 | Park | 348/665 |
| 2010/0245552 A1* | 9/2010 | Higuchi | 348/68 |
| 2010/0245616 A1* | 9/2010 | Yoshino et al. | 348/223.1 |
| 2010/0266202 A1 | 10/2010 | Minai | |
| 2011/0317004 A1* | 12/2011 | Tao | A61M 5/1684 348/135 |
| 2012/0013773 A1* | 1/2012 | Yoshino et al. | 348/241 |
| 2012/0218394 A1* | 8/2012 | Yoshino et al. | 348/65 |

FOREIGN PATENT DOCUMENTS

| | | |
|---|---|---|
| JP | 3559755 B2 | 9/2004 |
| JP | 2004-321244 A | 11/2004 |
| JP | 2007-236415 A | 9/2007 |
| JP | 2008-43604 A | 2/2008 |
| WO | WO 2010/050400 A1 | 5/2010 |

* cited by examiner ered with specific narrow wavelength band light (narrowband light) as observation light to obtain tissue information at a desired depth of the tissue of the living body.
IMAGE PROCESSING DEVICE

BACKGROUND OF THE INVENTION

The present invention relates to an image processing device capable of endoscopic imaging making use of the characteristics of both of a normal light observation image obtained with white light and a special light observation image obtained with specific narrowband light.

In recent years, use is made of an endoscope system capable of so-called special light observation in which a mucosal tissue of a living body is irradiated with specific narrow wavelength band light (narrowband light) as observation light to obtain tissue information at a desired depth of the tissue of the living body.

The special light observation can simply visualize biological information which is not obtainable from the image observed with normal light (white light), such as the microstructure in the superficial layer of a neovascular vessel formed in a mucosal layer or a submucosal layer, or an enhanced lesion. For example when a cancer lesion is to be observed, a mucosal tissue is irradiated with blue (B) narrowband light suitable to the observation of the tissue in the superficial layer and green (G) narrowband light suitable to the observation of the tissue in the middle and deep layers, whereby the state of the microvessels and microstructure in the superficial layer of the tissue can be more precisely observed and the lesion can be therefore more correctly diagnosed.

The endoscope system as described in JP 3559755 B is known as an endoscope system having the functions of normal light observation and special light observation.

The endoscope system uses a light source device which includes a light source for emitting white light and a rotary filter having an R filter for converting white light into red (R) light, a G filter for converting white light into green (G) light and a B filter for converting white light into blue (B) light, and an endoscope which captures images with an imaging device for measuring without separation of incident light. The endoscope system captures images in a so-called frame sequential manner.

The endoscope system described in JP 3559755 B uses the rotary filter of a double structure including a first set of outside filters and a second set of inside filters.

The first set of outside filters are filters for use in the normal light observation which have such spectral characteristics that the wavelength ranges of the respective colors overlap each other. On the other hand, the second set of inside filters are filters for use in the special light observation which have such discrete narrowband spectral characteristics that the wavelength ranges of the respective colors are separated from each other.

Therefore, this endoscope system is capable of both of the normal light observation and the special light observation by shifting the rotational axis of the rotary filter so that the first set of filters may act on the optical path when the normal light observation is performed and the second set of filters may act on the optical path when the special light observation is performed.

However, switching between the normal light observation and the special light observation in this endoscope system requires changeover of the rotary filter. Therefore, both of a normal light observation image and a special light observation image cannot be simultaneously observed in the same biological tissue.

Under the circumstances, various proposals have been made to enable a normal light observation and a special light observation to be performed simultaneously.

For example, JP 2004-321244 A describes an endoscope system (electronic endoscope system) which involves alternately capturing and storing normal light images and special light images at predetermined timings, reading out images at predetermined timings and subjecting the images to mutually different processing to acquire a normal light observation image and a special light observation image (substantially) simultaneously.

In this endoscope system, the normal light observation image and the special light observation image are observed simultaneously by displaying the two images acquired at the same period one by one, side by side on one screen or in an overlapping manner (composition of two images).

JP 2008-43604 A describes an endoscope system which processes a color image having R, G and B images captured in limited bands with a low-pass filter or a band-pass filter to generate image signals of a normal light observation image and those of a special light observation image thereby acquiring the normal light observation image and the special light observation image simultaneously.

In this endoscope system as well, the thus acquired normal light observation image and special light observation image are observed simultaneously by displaying the two images one by one or side by side on one screen.

SUMMARY OF THE INVENTION

The endoscope systems described in JP 2004-321244 A and JP 2008-43604 A can simultaneously display and observe a special light image and a normal light image in the same biological tissue.

However, according to the systems described in these documents, the special light observation image must be compared with the normal light observation image, which requires time and effort, and an endoscopic image making full of the characteristics of both of the normal light observation image and the special light observation image (e.g., the advantage of the special light observation image that microvessels in the superficial layer are easily observed and the advantage of the normal light observation image that the image is light and the structure and state of the whole image region including the depth direction can be easily recognized) is not obtained yet.

An object of the present invention is to solve the foregoing prior art problems and to provide an image processing device capable of acquiring a normal light observation image and a special light observation image captured with an endoscope simultaneously or substantially simultaneously and displaying an image making full use of the characteristics of the normal light observation image and the special light observation image.

In order to achieve the above object, the present invention provides an image processing device comprising:

an image acquisition unit for acquiring a normal light observation image captured by an endoscope using white light as observation light and a special light observation image captured by the endoscope simultaneously with the normal light observation image using predetermined narrowband light as the observation light; and an image processing unit for subjecting the normal light observation image acquired by the image acquisition unit to predetermined processing to generate a processed normal light observation image and providing information of the processed normal light observation image to the special light observation image.

In the image processing device of the invention, the image processing unit preferably performs frequency processing on the normal light observation image as the predetermined processing.

The image processing unit preferably has at least one function selected from a function of processing the normal light observation image with a low-pass filter and a function of processing the normal light observation image with a band-pass filter. The image processing unit preferably has a function of processing the normal light observation image with a low-pass filter, determining an average of the processed normal light observation image and extracting pixels in which a difference from the determined average is equal to or larger than a predetermined threshold. The image processing unit preferably has a function of processing the normal light observation image with a low-pass filter, determining a ratio between red, green and blue in each pixel of the processed normal light observation image and an average of the ratio between red, green and blue and extracting pixels in which a difference from the determined average of the ratio is equal to or larger than a predetermined threshold.

The image processing device of the invention acquires a normal light observation image captured with an endoscope using white light as observation light and a special light observation image captured with the endoscope (substantially) at the same time at the same position as for the normal light observation image and using specific narrowband light as observation light, subjects the normal light observation image to predetermined processing, and generates an image which includes information of the processed normal light observation image provided to the special light observation image by image composition or other processing.

Therefore, the image processing device of the invention provides the information of the normal light observation image having undergone frequency processing with, for example, a low-pass filter to the special light observation image, whereby an image can be generated in which information on the structure and state of the surface of a living body which is likely to be unclear in the special light observation or information on the deeper area in the observed field of view which is not easy to observe for lack of light quantity is provided to the special light observation image in which capillaries in the superficial layer and thick blood vessels in the middle and deep layers are advantageously reproduced.

Accordingly, the invention is capable of using a special light observation image and a normal light observation image captured simultaneously at the same position to generate and display an image making full use of the characteristics of the normal light observation image and the special light observation image, the image being obtained by providing the information of the normal light observation image in which the structure and state of the whole image region including the depth can be easily recognized, to the special light observation image serving as the base in which capillaries in the superficial layer and thick blood vessels in the middle and deep layers are advantageously reproduced.

DETAILED DESCRIPTION OF THE INVENTION

On the following pages, the image processing device of the invention is described in detail with reference to the preferred embodiments illustrated in the accompanying drawings.

Figure 1:
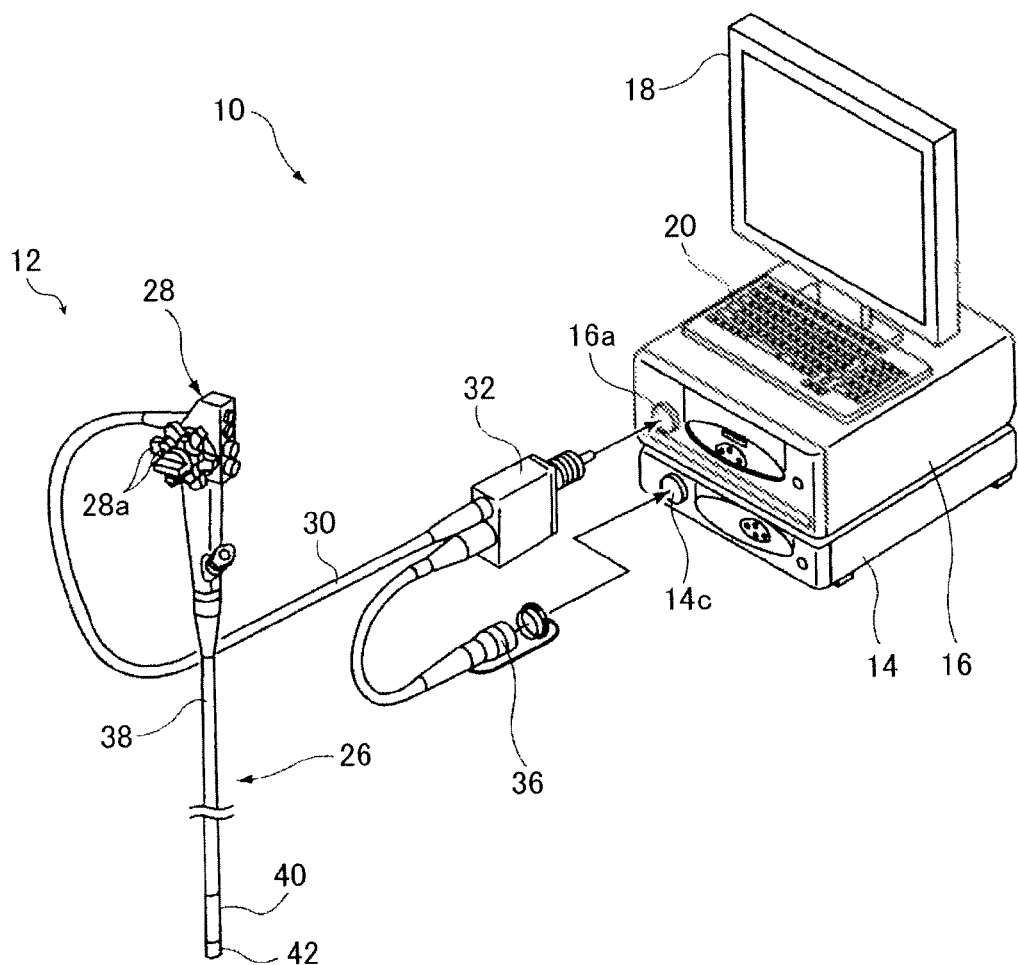
FIG. 1 is a conceptual diagram showing an embodiment of an endoscope system to which an image processing device of the invention is applied.
Figure 2:
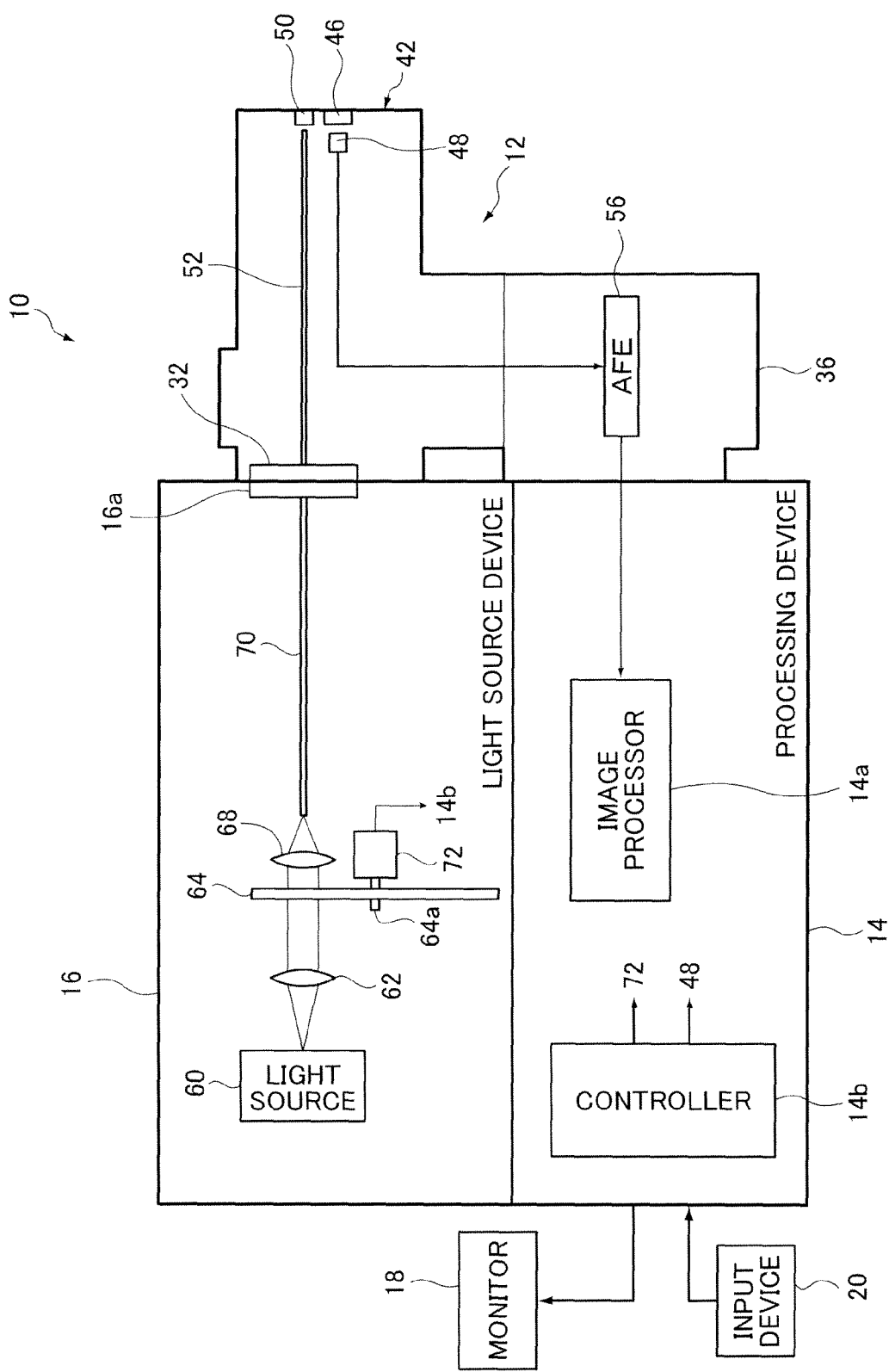
FIG. 2 is a conceptual block diagram showing the configuration of the endoscope system shown in FIG. 1.

FIG. 1 is a schematic perspective view showing an exemplary endoscope system which uses the image processing device of the invention and FIG. 2 conceptually shows the configuration of the endoscope system shown in FIG. 1.

The illustrated endoscope system 10 includes, for example, an endoscope 12, a processing device 14 for processing an image captured by the endoscope 12 and a light source device 16 for supplying observation light (illumination light) for use in observation and image capture using the endoscope 12.

The processing device 14 includes a monitor 18 for displaying an image captured by the endoscope and an input device 20 for inputting various instructions (the processing device 14 is connected to the monitor 18 and the input device 20). The processing device 14 may further include a printer (recording unit) for outputting an image captured by the endoscope as a hard copy.

In the illustrated endoscope system 10, the processing device 14 makes up the image processing device of the invention.

As shown in FIG. 2, the endoscope 12 is an electronic endoscope which photoelectrically captures an image using an imaging device such as a CCD sensor 48. As in a common endoscope, the endoscope 12 includes an insertion section 26, an operating section 28, a universal cord 30, a connector 32 and a video connector 36.

During the observation (diagnosis), the endoscope 12 is used with the video connector 36 and the connector 32 connected to a connecting portion 14c of the processing device 14 and a connecting portion 16a of the light source device 16, respectively. As in a common endoscope, the connector 32 is connected to a suction means and an air supply means for the suction from and the air supply to the site to be observed, and a water supply means for the water injection on the site to be observed.

As in a common endoscope, the insertion section 26 of the endoscope 12 includes a long flexible portion 38 on the proximal side, a distal scope portion (endoscope distal portion) 42 provided with the COD sensor 48 and the like, and a bending portion (angle portion) 40 located between the flexible portion 38 and the scope portion 42. The operating section 28 includes manipulation knobs 28a for bending the bending portion 40.

As schematically shown in FIG. 2, the scope portion 42 is provided with an imaging lens 46, the CCD sensor 48, an illumination lens 50, an optical fiber 52 and a cover glass (not shown) for protecting the lenses and the like.

Although not shown, the endoscope 12 is also provided with a forceps channel and a forceps port for inserting various treatment tools such as a forceps, and air supply/water supply channels and air supply/water supply ports for use in suction, air supply and water supply.

The forceps channel extends through the bending portion 40 and the flexible portion 38 to communicate with a forceps insertion port provided in the operating section 28, and the air supply/water supply channels extend through the bending portion 40, the flexible portion 38, the operating section 28 and the universal cord 30 to communicate with connecting portions with the suction means, the air supply means and the water supply means in the connector 32.

The optical fiber 52 extends through the bending portion 40, the flexible portion 38, the operating section 28 and the universal cord 30 and terminated by the connector 32 which is connected to the light source device 16.

Observation light emitted from the light source device 16 to be described later enters the optical fiber 52 through the connector 32 and propagates through the optical fiber 52. In the scope portion 42, the light enters the illumination lens 50 from the distal end of the optical fiber 52 and passes through the illumination lens 50 to be irradiated on an observation site.

The observation site having received the observation light is imaged through the imaging lens 46 on the light-receiving surface of the CCD sensor 48.

In the illustrated endoscope system 10, the CCD sensor 48 used in the endoscope 12 is a so-called monochrome COD sensor which captures light incident on the light-receiving surface without separating it into bands of R (red), B (blue) and G (green) colors. The CCD sensor 48 images the observation site by a so-called frame sequential process using R light, G light, B light and narrowband B light supplied from the light source device 16 to be described later as the observation light.

In the practice of the invention, the imaging device is not limited to the COD sensor 48 and various known imaging devices such as a CMOS image sensor may be used.

Output signals from the CCD sensor 48 are sent on signal lines from the scope portion 42 to the video connector 36 through the bending portion 40, the flexible portion 38, the operating section 28, the universal cord 30 and the connector 32.

In the illustrated embodiment, an AFE (Analog Front End) board 56 is disposed in the video connector 36.

The AFE board 56 includes, for example, a correlated double sampling circuit, an amplifier (automatic gain control circuit) and an A/D converter. In the AFE board 56, the output signals from the CCD sensor 48 are subjected to noise removal by correlated double sampling, amplification in the amplifier and conversion of analog signals into digital signals in the A/D converter, and then outputted to the processing device 14 (more specifically to a DSP 76 to be described later) as digital image signals.

In the endoscope system of the invention, these processing steps may be performed in the connector 32 or the processing device 14 instead of the video connector 36.

As described above, the connector 32 of the endoscope 12 in the endoscope system 10 is connected to the connecting portion 16a of the light source device 16.

The light source device 16 supplies the endoscope 12 with observation light for the internal observation of a living body. As described above, the observation light supplied from the light source device 16 toward the endoscope 12 enters the optical fiber 52 through the connector 32 and propagates therethrough to be irradiated on the observation site through the scope portion 42.

As schematically shown in FIG. 2, the light source device 16 of the endoscope system 10 includes a light source 60, a collimator lens 62, a rotary filter 64, a condenser lens 68, an optical fiber 70, a rotary drive source 72 and the connecting portion 16a.

The light source 60 is one for emitting light used for the observation.

In the light source device 16 of the illustrated endoscope system 10, various light sources capable of emitting white light that are used in known endoscope systems may be employed for the light source 60, as exemplified by a xenon lamp and a natural light LED.

White light emitted from the light source 60 is collimated by the collimator lens 62 into parallel light, which enters the rotary filter (filter turret) 64.

Figure 3A:
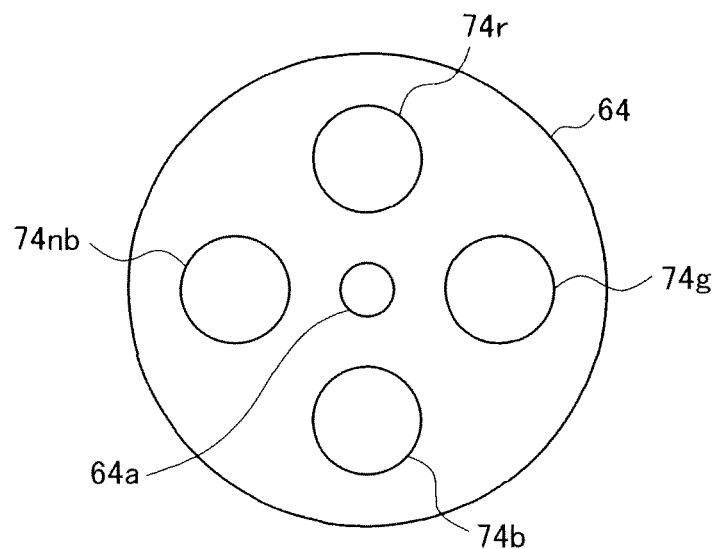
FIGS. 3A and 3B are conceptual diagrams showing exemplary rotary filters used in the endoscope system shown in FIG. 1.

FIG. 3A is a conceptual diagram showing the rotary filter 64. The rotary filter 64 includes four filters such as an R filter 74r for converting white light into R light, a G filter 74g for converting white light into G light, a B filter 74b for converting white light into B light and a narrowband B filter 74nb for converting white light into narrowband B light.

The R, G and B filters are known color filters that may be used to take a color image by separating the image into components of three primary colors of red, green and blue.

The narrowband B light is, for example, light with a wavelength of 380 to 480 nm and a bandwidth in spectral distribution of 75 nm or less. Specifically various types of narrowband B light used in so-called special light observation (narrowband light observation) in the endoscope, more specifically light with a wavelength of 390 to 445 nm and particularly light with a wavelength of 400±10 nm and a central wavelength of 405 nm may be used.

Various filters which can convert white light into such narrowband B light (hereinafter referred to as "narrowband B light") may be used for the narrowband B filter 74nb.

The rotary drive source 72 which is controlled for the drive (rotation) by the controller 14b of the processing device 14 to be described later causes the rotary filter 64 to rotate about a rotary shaft 64a to sequentially insert the filters in the optical path of light having passed through the collimator lens 62.

In other words, white light emitted from the light source 60 is separated by the inserted filters of the rotary filter 64 into R light, G light, B light and narrow-band B light in a time-sharing manner.

Light having passed through the filters of the rotary filter 64 is condensed by the condenser lens 68 and the condensed light impinges on the incident end face of the optical fiber 70.

The light having entered the optical fiber 70 propagates therethrough and passes through the connecting portion 16a and the connector 32 of the endoscope 12 to enter the optical fiber 52 of the endoscope 12. Then, the light propagates through the optical fiber 52 and is irradiated from the scope portion 42 on the observation site as observation light and the CCD sensor 48 captures an image of the observation site.

As described above, the light source device 16 uses the rotary filter 64 to separate white light from the light source 60 into R light, G light, B light and narrowband B light in a time sharing manner and supplies them as the observation light. Therefore, the R light, G light, B light and narrowband B light are sequentially and repeatedly supplied to the endoscope 12 and are then irradiated from the scope portion 42 on the observation site.

Under the control of the controller 14b, the CCD sensor 48 sequentially captures (samples) images for the light of the respective colors in synchronization with the rotary filter 64 (at a timing suitable for the rotation of the rotary filter 64). That is, the monochrome CCD sensor 48 captures an R image, a G image, a B image and a narrowband B image in a frame sequential manner upon the irradiation with the R light, G light, B light and narrowband B light, respectively.

The processing device 14 of the endoscope system 10 obtains from the R image, G image and B image a normal light observation image using white light as the observation light and from the narrowband B image and G image a special light observation image using special light as the observation light. In other words, the endoscope system 10 can obtain a normal light observation image and a special light observation image which are taken simultaneously or substantially simultaneously. This point will be described in detail later.

In the light source device 16 used in the illustrated endoscope system 10, the rotary filter 64 is not limited to a type having four filters as shown in FIG. 3A.

Figure 3B:
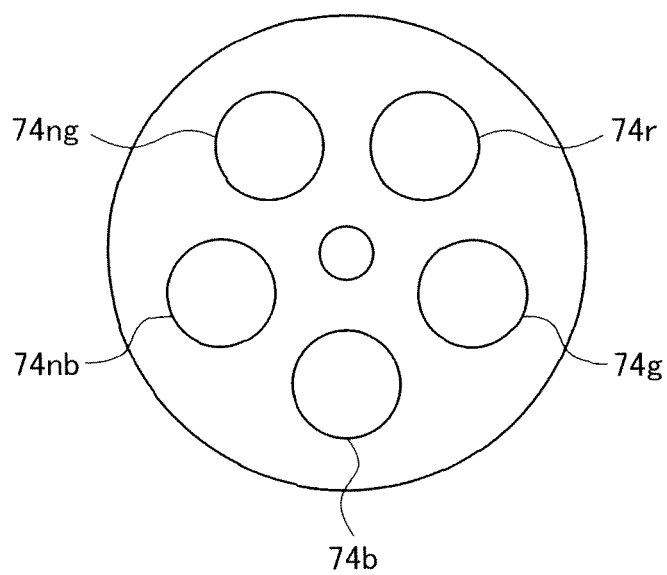

For example, a rotary filter having five filters as shown in FIG. 3B may also be advantageously used which includes a narrowband G filter 74ng for converting white light into narrowband G light in addition to the R filter 74r, the G filter 74g, the B filter 74b and the narrowband B filter 74nb.

In this case, the processing device 14 obtains from the R image, G image and B image a normal light observation image using white light as the observation light and from the narrowband B image and narrowband G image obtained from the narrowband G light a special light observation image using special light as the observation light.

The narrowband G light is, for example, light with a wavelength of 480 to 580 nm and a bandwidth in spectral distribution of 75 nm or less. Specifically various types of narrowband G light used in so-called special light observation and more specifically light with a wavelength of 530 to 550 nm may be used.

Various filters which can convert white light into such narrowband G eight (hereinafter referred to as "narrowband G light") may be used for the narrowband G filter 74ng.

The observation site having received the observation light from the light source device 16 is imaged by the CCD sensor 48.

As described above, the image captured by the COD sensor 48 (output signals from the COD sensor 48) is subjected to processing such as A/D conversion in the AFE board 56 and supplied to the processing device 14 as digital image signals (image data/image information).

The processing device 14 subjects the image signals supplied (outputted) from the endoscope 12 (the image signals are also referred to simply as an "image") to predetermined processing so that the monitor 18 displays them as an image captured by the endoscope 12 and also controls the endoscope system 10. The processing device 14 includes an image processor 14a and a controller 14b for controlling the whole of the endoscope system 10 including the processing device 14.

Figure 4:
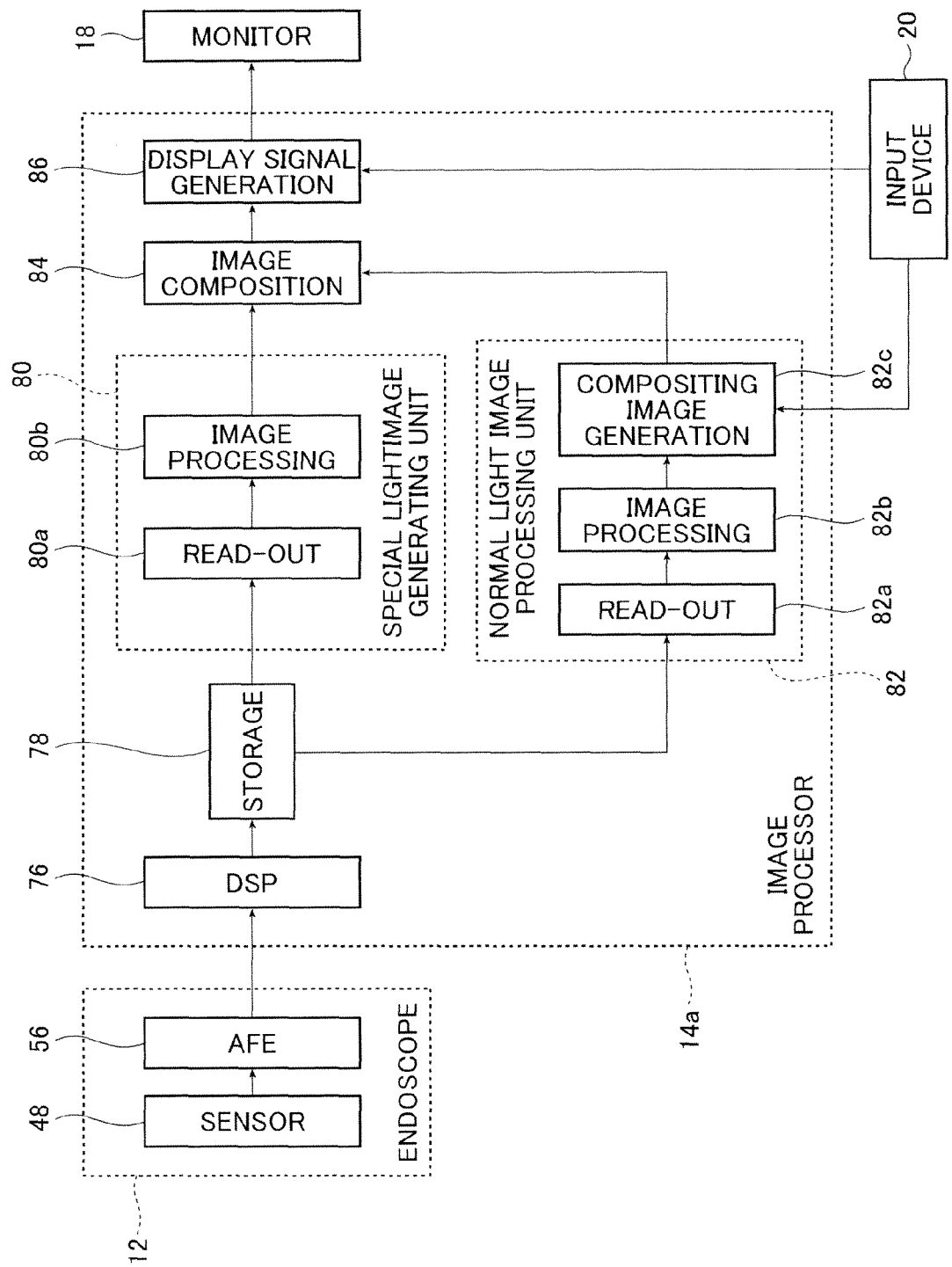
FIG. 4 is a conceptual block diagram showing a processor of the endoscope system shown in FIG. 1.

FIG. 4 is a conceptual block diagram showing the image processor 14a of the processing device 14.

As shown in FIG. 4, the image processor 14a includes the DSP 76, a storage unit 78, a special light image generating unit 80, a normal light image processing unit 82, an image composition unit 84 and a display signal generating unit 86.

In the processing device 14, images (R image, G image, B image and narrowband B image) from the endoscope 12 are supplied to the DSP 76.

The DSP 76 is a known type of DSP (Digital Signal Processor), where the supplied images are subjected to predetermined processing steps such as gamma correction and color correction. The processed images are then stored in a predetermined region of the storage unit (memory) 78.

Once the images are stored in the storage unit 78, the special light image generating unit 80 reads out the narrowband B image and G image from the storage unit 78 to generate a special light observation image. The normal light image processing unit 82 reads out the R, G and B images from the storage unit 78 to generate a normal light observation image, from which a compositing image for the composition with the special light observation image is generated.

As described above, the R, G, B and narrowband B images are images simultaneously taken by rotating the rotary filter 64 and therefore the special light observation image and the normal light observation image are simultaneously taken images.

The special light image generating unit 80 includes a read-out section 80a and an image processing section 80b.

As described above, the read-out section 80a is a section in which the narrowband B image and the G image forming the special light observation image are read out from the images of the respective colors stored in the storage unit 78 and supplied to the image processing section 80b.

When the rotary filter of the light source device 16 has five filters including the narrowband G filter 74ng as shown in FIG. 3B, five images including the R image, G image, B image, narrowband B image and narrowband G image are supplied from the endoscope 12.

In this case, the read-out section 80a does not read out the G image. The read-out section 80a reads out the narrowband B image and the narrowband G image from the storage unit 78 as the images for forming the special light observation image and supplies them to the image processing section 80b. The following processing steps in the special light image generating unit 80 are performed on the narrowband G image instead of the G image.

The image processing section 80b is a section in which the narrowband B image and the G image are processed to obtain the special light observation image.

On the displayed image (image outputted from the processing device 14), three sub-pixels of R, G and B make up one pixel. In the illustrated embodiment, however, the special light observation image is only obtained from the narrowband B image and the G image. Therefore, the image processing section 80b first allocates the G image to R pixels corresponding to the display and the narrowband B image to G pixels and B pixels corresponding to the display to form an image in which three sub-pixels of R, G and B corresponding to the display make up one pixel.

The image allocation may be optionally preceded by image processing or correction such as multiplication of an image by a predetermined coefficient.

The image processing section 80b subjects the images allocated to the R, G and B pixels to processing with a 3×3 matrix, gradation conversion, processing with a three-dimensional LUT or other color conversion processing; color enhancement for giving a color difference between a blood vessel and a mucous membrane on the screen by enhancing in a direction in which the color difference between the blood vessel and the mucous membrane is to be more accentuated than the average colors of the image so that the blood vessel can be more easily seen; and image structure enhancement such as sharpening and edge enhancement, and supplies the processed image to the image composition unit 84 as the special light observation image.

On the other hand, the normal light image processing unit 82 includes a read-out section 82*a*, an image processing section 82*b* and a compositing image generating section 82*c*.

As described above, the read-out section 82*a* is a section in which the R, G and B images forming the normal light observation image are read out from the images of the respective colors stored in the storage unit 78 and supplies them to the image processing section 82*b*.

The image processing section 82*b* subjects the R, G and B images to processing with a 3×3 matrix, gradation conversion, processing with a three-dimensional LUT or other color conversion processing; color enhancement for giving a color difference between a blood vessel and a mucous membrane on the screen by enhancing in a direction in which the color difference between the blood vessel and the mucous membrane is to be more accentuated than the average colors of the image so that the blood vessel can be more easily seen; and image structure enhancement such as sharpening and edge enhancement, and supplies the processed image to the compositing image generating section 82*c* as the normal light observation image.

The compositing image generating section 82*c* is a section in which the normal light observation image formed in the image processing section 82*b* is subjected to predetermined processing to generate the compositing image for compositing with the special light image generated in the special light image generating unit 80 (compositing image for providing information of the normal light observation image to the special light observation image) and supplies the compositing image to the image composition unit 84.

In the illustrated embodiment, the compositing image generating section 82*c* subjects the normal light observation image generated by the image processing section 82*b* to, for example, frequency processing using a low-pass filter (LPF), a band-pass filter (BPF) or the like to generate the compositing image.

As is well known, according to the special light observation using narrowband B light and G light (preferably narrowband G light), microvessels in the superficial layer of the mucous membrane and thick blood vessels in the middle and deep layers of the mucous membrane can be imaged (information on these blood vessels can be obtained).

On the other hand, in the special light observation image, the use of narrowband light reduces the quantity of light and the deeper area in the observed field of view gets darker, whereby image information may not be obtained for lack of light quantity depending on the shooting place. Since the observation is made with narrowband B light and (narrowband) G light, it is hard to visually recognize the structure and state of the observed biological surface (e.g., roughened biological surface).

In contrast, the normal light observation image can be captured with a large quantity of white light and therefore the entire observed field of view including the depth direction can be imaged with a sufficient quantity of light. Since imaging is made with white light, the structure and state of the biological surface including the roughened biological surface are also easily recognized visually in the image obtained.

Therefore, in the image obtained by processing the normal light observation image with an LPF or a BPF which passes low frequencies within a predetermined frequency band, microvessels in the superficial layer and thick blood vessels in the middle and deep layers which are advantageously observable in the special light observation image are removed and information on the deeper area in the observed field of view and information on the structure and state of the biological surface (e.g., roughened biological surface) are kept intact.

Therefore, by compositing the thus processed normal light observation image serving as the compositing image with the special light observation image, an image which makes full use of the characteristics of the normal light observation image and the special light observation image can be generated. The resulting image includes the special light observation image having microvessels in the superficial layer and thick blood vessels in the middle and deep layers, and the information of the normal light observation image in which the structure and state of the whole image region including the depth are reproduced.

In the practice of the invention, processing performed in the compositing image generating section 82*c* to generate the compositing image from the normal light observation image is not limited to one type. More specifically, the compositing image generating section 82*c* may have a plurality of filters such as a plurality of types of filters (e.g., LPF and BPS) or a plurality of types of LPFs or the like having different passbands so that a filter to be used is appropriately selected to process the normal light observation image thereby generating the compositing image.

A plurality of different types of processing (e.g., composition of an image processed with an LPF and an image processed with a BPF or processing with a filter selected from a plurality of types of LPFs or BPFs having different passbands) may be prepared as selectable steps so that a processing step in the compositing image generating section 82*c* (compositing image to be prepared) can be appropriately selected in accordance with the desired image quality (image) using an instruction/input means provided in the input device 20 or optionally in the operating section 28 of the endoscope 12.

Frequency processing using such filters may be combined with various arithmetic processing steps to generate a compositing image.

An exemplary processing step involves processing a normal light observation image with an LPF, determining the average of the image obtained by the LPF processing and extracting pixels in which the difference from the determined average is equal to or larger than an appropriately set threshold to obtain an image composed of the extracted pixels as a compositing image.

Another exemplary processing step involves processing a normal light observation image with an LPF, determining the ratio between R, G and B in each pixel and the average of the ratio for the image obtained by the LPF processing and extracting pixels in which the difference from the determined average of the ratio is equal to or larger than an appropriately set threshold to obtain an image composed of the extracted pixels as a compositing image.

The compositing images generated by performing such processing steps are both images obtained in consideration of the difference from the average in the image and therefore in the compositing images that can be obtained, microvessels in the superficial layer and blood vessels in the middle and deep layers are removed, the information on the deeper area in the observed field of view is fully ensured, and a site having a change in the structure and state of the biological surface including irregularities can be more advantageously detected.

The compositing image generating section 82c may have a function of generating one or more than one type of compositing image by the foregoing frequency processing (and optionally composition), a function of generating a compositing image using the average of an image processed with an LPF, and a function of generating a compositing image using the RGB ratio in an image processed with an LPF so that one of the methods for generating a compositing image can be selected as above.

The compositing image generating section 82c subjects the normal light observation image to predetermined processing such as frequency processing to generate a compositing image and supplies it to the image composition unit 84.

The image composition unit 84 composites the compositing image supplied from the normal light image processing unit 82 with the special light observation image supplied from the special light image generating unit 80 to obtain a composite image and supplies the display signal generating unit 86 with the composite image for displaying on the monitor 18.

The image composition method in the image composition unit 84 is not particularly limited and various known image composition methods may be used.

As is well known, in the image captured in the special light observation, microvessels in the superficial layer is bluish and blood vessels in the middle and deep layers are greenish. In other words, the special light observation image has different colors from those of the actual body and may provide a feeling of unnaturalness or strangeness.

Therefore, prior to the composition of the compositing image with the special light observation image, microvessels in the superficial layer and blood vessels in the middle and deep layers may be optionally extracted from the special light observation image to perform color conversion so that the colors of the image coincide with the original colors of the body.

Color conversion may be performed by known methods such as color correction and density correction. Microvessels in the superficial layer and blood vessels in the middle and deep layers may be extracted by frequency processing using, for example, a high-pass filter (HPF) or a BPF having a higher-frequency passband.

The special light observation image may be processed in the display signal generating unit 86 or in the image processing section 80b of the special light image generating unit 80. In addition, whether or not color conversion of the special light observation image is performed may be selectable.

The display signal generating unit 86 subjects the composite image supplied from the image composition unit 84 to color space conversion, scaling and other necessary processing steps, or image allocation, incorporation of character information such as the name of a subject and other necessary processing steps to generate a display image having the composite image incorporated therein and this image is displayed on the monitor 18.

The display signal generating unit 86 may receive not only the composite image but also images from the special light image generating unit 80 and the normal light image processing unit 82 in response to an instruction given from the indication means provided in the input device 20 or the operating section 28 of the endoscope 12 so that the monitor 18 may display not only the composite image but also the normal light observation image and the special light observation image.

In this case, the monitor 18 may display all the images, two or more appropriately selected images, or one appropriately selected image. In addition, display modes such as three-image display, two-image display, and toggle image display are available.

An example of the operation of the endoscope system 10 is described below.

When the input device 20 issues an instruction for the start of imaging with the endoscope 12, the light source 60 of the light source device 16 is turned on, the rotary drive source 72 starts to rotate the rotary filter 64, and the CCD sensor 48 starts imaging (photometry) in synchronization with the rotation of the rotary filter 64.

Light emitted from the light source 60 is collimated by the collimator lens 62, separated by the rotary filter 64 in a time sharing manner into R light, G light, B light and narrowband B light (and optionally narrowband G light), and enters the optical fiber 70 through the condenser lens 68.

The optical fiber 70 propagates the incident light which is supplied through the connecting portion 16a to the connector 32 of the endoscope 12 as observation light.

The observation light supplied to the connector 32 of the endoscope 12 propagates through the optical fiber 52 to the scope portion 42, where the observation light is emitted from the distal end of the optical fiber 52 to be irradiated through the illumination lens 50 on the observation site in the living body.

The observation site having received the observation light is imaged through the imaging lens 46 on the light-receiving surface of the COD sensor 48, which captures an R image, a G image, a B image and a narrowband B image in a frame sequential manner (performs photometry).

Output signals from the CCD sensor 48 are supplied to the APE board 56. The APE board 56 subjects the output signals from the CCD sensor 48 to noise removal by correlated double sampling, amplification and A/D conversion to obtain digital image signals, which are then supplied to the DSP 76 of the processing device 14 (processor 14a).

The DSP 76 subjects the supplied image (image signals) to predetermined processing such as gamma correction and color correction and stores the processed image in a predetermined portion of the storage unit 78.

Once the image signals are stored in the storage unit 78, the read-out section 80a of the special light image generating unit 80 reads out the narrowband B image and the G image from the storage unit 78 and supplies them to the image processing section 80b. The read-out section 82a of the normal light image processing unit 82 reads out the R image, G image and B image from the storage unit 78 and supplies them to the image processing section 82b.

In the special light image generating unit 80, the image processing section 80b allocates the G image to R pixels to be displayed and the narrowband B image to B and G pixels to be displayed to form pixels each composed of three sub-pixels, and the image is further subjected to color conversion, color enhancement and image structure enhancement. The resulting image is supplied to the image composition unit 84 as the special light observation image.

On the other hand, in the normal light image processing unit 82, the image processing section 82b performs color conversion, color enhancement and image structure enhancement and supplies the resulting normal light observation image to the compositing image generating section 82c.

The compositing image generating section 82c processes the normal light observation image supplied thereto with, for example, an LPF to generate a compositing image.

Once the compositing image is generated, the compositing image generating section 82c supplies the thus generated compositing image to the image composition unit 84.

The image composition unit 84 composites the special light observation image supplied from the special light image generating unit 80 with the compositing image supplied from the normal light image processing unit 82 to generate a composite image in which information of the normal light observation image (information on the deeper area in the observed field of view and information on the structure and state of the biological surface such as the roughened surface) is provided to the special light observation image, and supplies the composite image to the display signal generating unit 86.

The display signal generating unit 86 generates a display image in which the composite image supplied thereto is incorporated and the monitor 18 displays the display image.

In the foregoing embodiment, the image processing device of the invention is applied to the endoscope system 10 which includes the light source device 16 using the rotary filter 64 with the filters for R light, G light, B light and narrowband B light, and the endoscope 12 using the monochrome COD sensor 48. However, this is not the sole case of the invention.

That is, the image processing device of the invention (the illustrated processing device 14) can be applied to various endoscope systems which use a light source device and an endoscope capable of capturing images used for a normal light observation image and a special light observation image simultaneously or substantially simultaneously.

For example, in the endoscope system 10 shown in FIGS. 1 and 2, another configuration is possible in which the light source device 16 has no rotary filter and the monochrome CCD sensor 48 used as the CCD sensor of the endoscope 12 is replaced by a four-color (five-color) COD sensor which separates incident light into R light, G light, B light and narrowband B light (and optionally narrow-bang G light) for simultaneous photometry, thereby capturing an R image, a G image, a B image and a narrowband B image and obtaining simultaneously captured normal light observation image and special light observation image as in the above embodiment.

In the endoscope system 10 shown in FIGS. 1 and 2, still another configuration is possible in which the rotary filter 64 of the light source device 16 is replaced by a rotary filter which has in its rotational direction a colorless transparent filter or a hole and a narrowband B filter converting white light into narrowband B light, and the monochrome CCD sensor 48 of the endoscope 12 is replaced by a common color CCD sensor.

The common color CCD sensor is a sensor which is used in a common endoscope or digital camera and separates incident light into R light, G light and B light of three primary colors for simultaneous photometry.

According to this configuration, the light source device rotates the rotary filter to alternately supply to the endoscope white light having passed through the colorless transparent filter and narrowband B light having passed through the narrowband B filter. In synchronization with the rotation of the rotary filter, the color COD sensor of the endoscope alternately captures a normal light observation image including an R image, a G image and a B image and using white light as observation light and a narrowband B image using narrowband B light as observation light.

The storage unit 78 of the processing device 14 thus stores the simultaneously captured R, G, B and narrowband B images as in the foregoing embodiment.

Therefore, the special light image generating unit 80 and the normal light image processing unit 82 likewise read out the R, G and B images, and the narrowband B image and G image from images stored in the storage unit 78, respectively, thereby obtaining simultaneously (substantially simultaneously) captured normal light observation image and special light observation image.

In this configuration as well, the rotary filter may further include a narrowband G filter in addition to the colorless transparent filter and the narrowband B filter so that a special light observation image is generated from the narrowband B image and the narrowband G image as in the foregoing embodiment.

Figure 5:
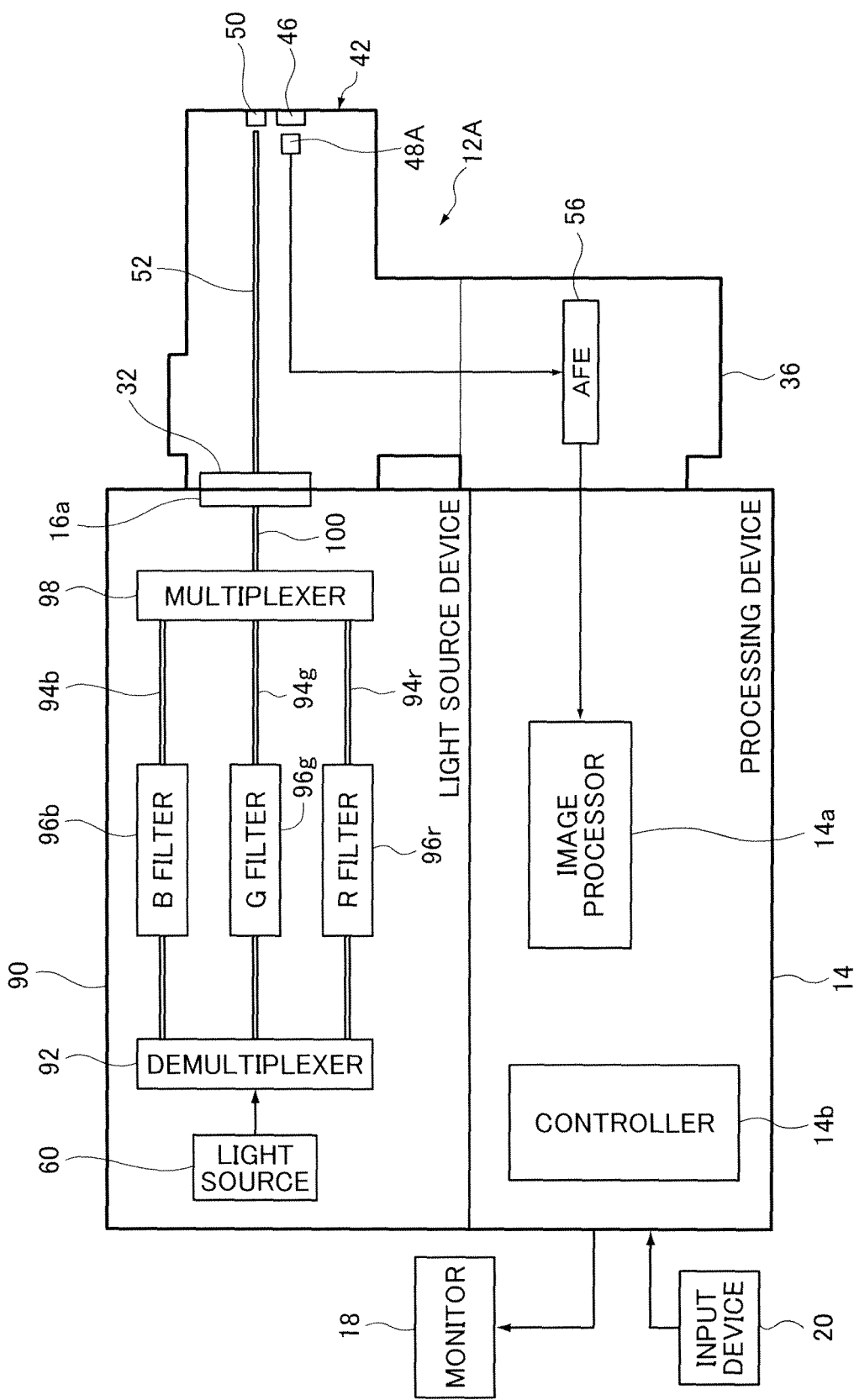
FIG. 5 is a conceptual block diagram showing the configuration of another embodiment of the endoscope system according to the invention.

The configuration using a light source device 90 as shown in FIG. 5 is another example which also uses an endoscope having a common color CCD sensor.

In FIG. 5, like components are denoted by the same reference numerals as in FIG. 2 and the following description mainly focuses on the different features. In an endoscope shown by reference numeral 12A, a CCD sensor 48A is not a monochrome CCD sensor but is the foregoing common color CCD sensor.

The light source device 90 includes the light source 60 which is the same as that used in the above embodiment, a demultiplexer 92, a B fiber 94b, a G fiber 94g, an R fiber 94r, a B filter 96b, a G filter 96g, an R filter 96r, a multiplexer 98, an optical fiber 100 and the connecting portion 16a which is the same as that used in the above embodiment.

In the illustrated light source device 90, white light emitted from the light source 60 is separated by the demultiplexer 92 into three components, which enter the optical fibers including the B fiber 94b, G fiber 94g and R fiber 94r and are propagated therethrough to the multiplexer 98.

The B filter 96b, the G filter 96g and the R filter 96r are provided between the demultiplexer 92 and the multiplexer 98 in the B fiber 94b, G fiber 94g and R fiber 94r, respectively. Entry of light in the filters from the optical fibers and exit of light from the filters to the optical fibers may be performed by any known method.

The B filter 96b is a filter for converting white light into narrowband B light. The G filter 96g is a filter for converting white light into narrowband G light or G light. The R filter 96r is a filter for converting white light into R light.

Therefore, the light propagated through the B fiber 94b is converted by the B filter 96b into narrowband B light, the light propagated through the G fiber 94g is converted by the G filter 96g into narrowband G light, and the light propagated through the R fiber 94r is converted by the R filter 96r into R light. The narrowband B light, the narrowband G light and the R light then enter the multiplexer 98.

The narrowband B light, the narrowband G light and the R light are converged in the multiplexer 98, propagated through the optical fiber 100 and supplied through the connecting portion 16a to the endoscope 12A.

In other words, the endoscope is supplied with pseudo white light which is a mixture of the narrowband B light, the narrowband G light and the R light and captures images using the pseudo white light as the observation light.

As described above, the CCD sensor of the endoscope is a color CCD sensor. Therefore, an R image, a G image and a B image are outputted from the endoscope and stored in the storage unit 78 of the processing device 14.

The observation light used is pseudo white light which is a mixture of the narrowband B light, the narrowband G light and the R light, and the CCD sensor 48A is a color CCD sensor. Therefore, the B image, G image and R image captured by the CCD sensor 48A can be used to generate a normal light observation image which uses white light as the observation light.

The B light and G light used for the observation are both narrowband. Therefore, the B image and G image captured by the CCD sensor 48A can be used to generate a special light observation image which uses the narrowband B light and narrowband G light as the observation light.

Therefore, the special light image generating unit 80 and the normal light image processing unit 82 read out the G and B images and the R, G and B images from images stored in the storage unit 78, respectively, whereby simultaneously captured normal light observation image and special light observation image can be obtained.

In the light source device 90 shown in FIG. 5, it is preferred to provide between the filters and the multiplexer 98 light quantity adjusting means which are each independently capable of adjusting the quantity of light and to supply each light to the multiplexer 98 so that a relation of B light>G light>R light is met for the quantity (intensity) of light.

In a common color CCD sensor, pixels of B, G and R colors have sensitivity until the neighboring color area owing to the filtering characteristics of the B, G and R colors. In other words, G pixels allow for the incidence and photometry of the narrowband G light and R-band light, and B pixels allow for the incidence and photometry of the narrowband B light and narrowband G light.

In contrast, by adjusting the quantity of light so that the relation of B light>G light>R light is met, the narrowband B light may predominantly enter the B pixels of the CCD sensor and the narrowband G light may likewise predominantly enter the G pixels. A proper normal light observation image and a proper special light observation image can be thus generated from the images read by the CCD sensor.

In cases where the quantity of light used for the observation meets the relation of B light>G light>R light, the images are preferably first subjected to gain adjustment in the normal light image processing unit 82 to obtain the same images as those captured with white observation light in which the B light, G light and R light are equal in quantity.

Amplification of the G image and the R image and reduction of the B image and the G image may be performed by gain adjustment using, for example, multiplication by a correction coefficient or processing with an LUT so as to obtain the same images as those captured with white observation light in which the B light, G light and R light are equal in quantity.

Figure 6:
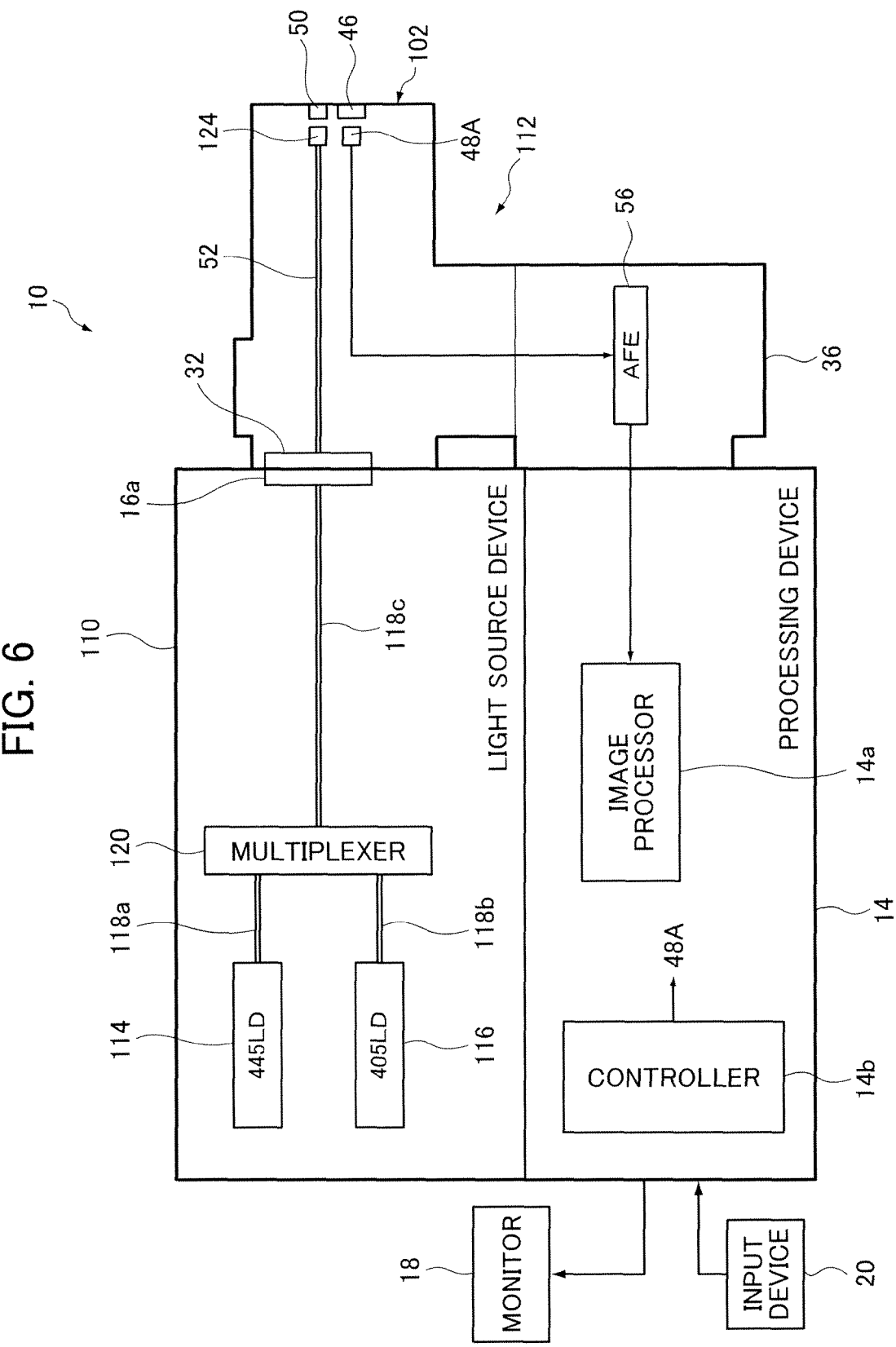
FIG. 6 is a conceptual block diagram showing the configuration of still another embodiment of the endoscope system according to the invention.

The configuration using a light source device 110 and an endoscope 112 as shown in FIG. 6 is still another example which also uses an endoscope having a common color CCD sensor.

In FIG. 6, like components are denoted by the same reference numerals as in FIG. 5 and the following description mainly focuses on the different features.

The light source device 110 includes a 445LD 114, a 405LD 116, optical fibers 118a, 118b and 118c, and a multiplexer 120.

Figure 7:
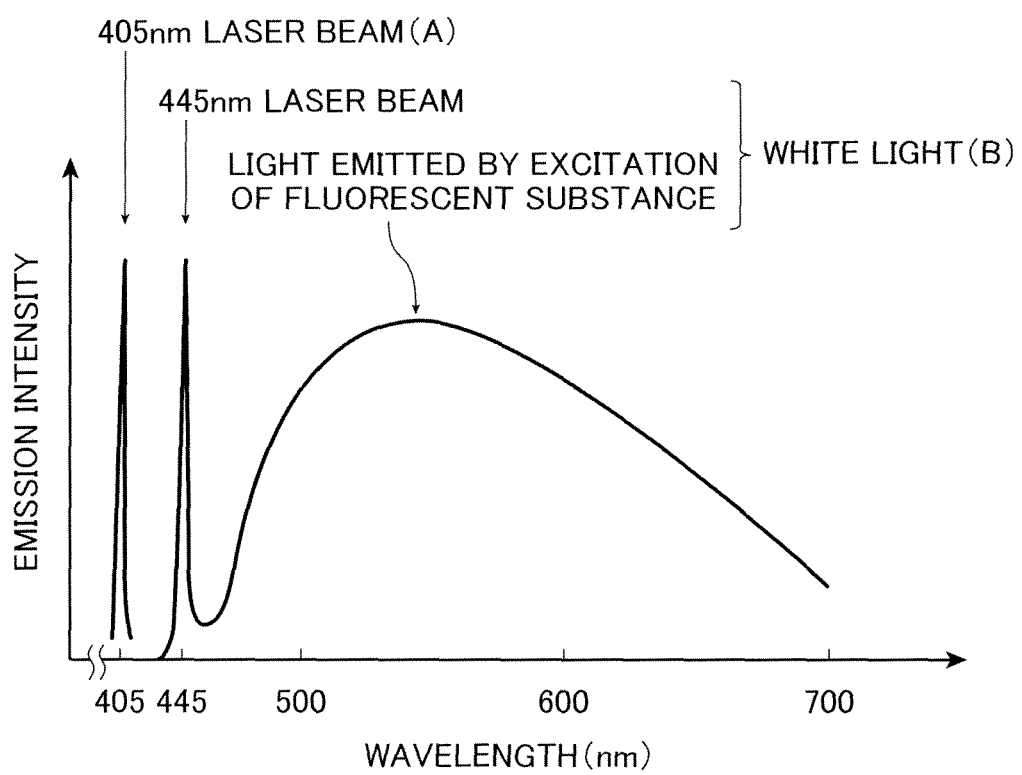
FIG. 7 is a conceptual diagram showing an exemplary spectrometric profile of observation light in the endoscope system shown in FIG. 6.

The 445LD 114 is a light source emitting B laser beams with a central wavelength of 445 nm having the spectrometric profile shown in FIG. 7. On the other hand, the 405LD 116 is a light source emitting narrowband blue-violet (V) laser beams with a central wavelength of 405 nm having the spectrometric profile shown in FIG. 7.

The B light emitted from the 445LD 114 is propagated through the optical fiber 118a and the V light emitted from the 405LD 116 is propagated through the optical fiber 118b and the B light and V light are multiplexed into a single beam by the multiplexer 120.

The B light and V light are multiplexed into the single beam, which is propagated through the optical fiber 118c, is supplied through the connecting portion 16a to the connector 32 of the endoscope 112, and enters and is propagated through the optical fiber 52 to exit from the distal end of the optical fiber 52.

In the endoscope 112, a fluorescent substance 124 is disposed at the distal end of the optical fiber 52. The fluorescent substance 124 includes a plurality of kinds of phosphors (e.g., YAG phosphor and BAN (BaMgAl$_{10}$O$_{17}$) phosphor) which absorb part of B light, excite and emit green to yellow light. The green to yellow light emitted by excitation of the fluorescent substance having absorbed B light as excitation light is combined with B light which was not absorbed in the fluorescent substance 124 but passed therethrough to form pseudo white light.

Most of the V light (V laser beams) emitted from the 405LD 116 passes through the fluorescent substance 124 without being absorbed therein.

FIG. 7 shows emission spectral characteristics of the V light emitted from the 405LD 116, the B light emitted from the 445LD 114 and the light emitted from the fluorescent substance 124 excited by the B light.

As shown in FIG. 7, the V light emitted from the 405LD 116 is narrowband V light represented by an emission line with a central wavelength of 405 nm (profile A).

The B light emitted from the 445LD 114 is represented by an emission line with a central wavelength of 445 nm. In addition, the light emitted from the fluorescent substance 124 excited by the B light has a spectral intensity distribution which shows an increase in emission intensity in a wavelength range of about 450 nm to about 700 nm.

Therefore, when only the 445LD 114 is turned on in the light source device 110, the light emitted by the excitation of the fluorescent substance 124 is combined with the B light from the 445LD 114 which was not absorbed in the fluorescent substance 124 to form pseudo white light (profile B), which enables normal light observation using white light as the observation light.

When both of the 445LD 114 and the 405LD 116 are turned on, narrowband V light shown by profile A is added to the observation light, thus enabling imaging with special light.

More specifically, the 405LD 116 in the light source device 110 is turned on and off in a predetermined period (or high power lighting and low power lighting are alternately repeated) under the control of the controller 14b so that images are captured by the CCD sensor 48A of the endoscope 112 in synchronization with the on/off status of the 405LD 116.

Accordingly, the special light image generating unit 80 reads out the G and B images from images stored in the storage unit 78 when the 405LD 116 is turned on (at the time of high power lighting) and the normal light image processing unit 82 reads out the R image, the B image and the G image from the images stored in the storage unit 78 when the 405LD 116 is turned off (at the time of low power lighting), thus enabling simultaneously (substantially simultaneously) captured normal light observation image and special light observation image to be obtained.

In this embodiment, the 405LD 116 is not turned on and off but is always turned on to generate a composite image so that simultaneously captured normal light observation image and special light observation image may be obtained as above.

While the image processing device of the invention has been described above in detail, the invention is by no means limited to the above embodiments, and various improvements and modifications may of course be made without departing from the spirit of the invention.

What is claimed is:

1. An image processing device comprising:
   an image acquisition unit for acquiring a normal light observation image captured by an endoscope using white light as observation light and a special light observation image captured by the endoscope simultaneously with the normal light observation image using predetermined narrowband light as the observation light; and
   an image processing unit for subjecting the normal light observation image acquired by the image acquisition unit to predetermined processing to generate a processed normal light observation image and compositing information of the processed normal light observation image with the special light observation image,
   wherein the image processing unit has a function of:
      processing the normal light observation image with a low-pass filter to generate the processed normal light observation image;
      determining a ratio between red, green and blue in each pixel of the processed normal light observation image and an average of the ratio between red, green and blue;
      extracting pixels in which a difference from the determined average of the ratio is equal to or larger than a predetermined threshold; and
      compositing an image composed of the extracted pixels with the special light observation image.

2. The image processing device according to claim 1, wherein the image processing unit generates the processed normal light observation image in which microvessels in a superficial layer and thick blood vessels in middle and deep layers are removed and information on a deeper area in an observed field of view and information on a structure and a state of a biological surface are kept intact.

3. The image processing device according to claim 1, wherein the image processing unit comprises a plurality of filters having different passbands, and the processing of the normal light observation image comprises using the plurality of filters.

4. The image processing device according to claim 3, wherein the processing of the normal light observation image comprises a plurality of different types of processing with the plurality of filters, the plurality of different types of processing being selectable in accordance with a desired image quality.

5. An endoscope system comprising:
   the image processing device according to claim 1.

* * * * *